US010638967B2

(12) United States Patent
Yanagi

(10) Patent No.: US 10,638,967 B2
(45) Date of Patent: May 5, 2020

(54) HANDHELD RADIO DEVICE FOR ASSESSING COGNITIVE, AUDITORY, VISUAL, AND SPEECH FUNCTION

(71) Applicant: Office of Intellectual Property, Code 36000, San Diego, CA (US)

(72) Inventor: Matthew A. Yanagi, Jamul, CA (US)

(73) Assignee: United States of America as represented by the Navy, Washington, DC (US)

( * ) Notice: Subject to any disclaimer, the term of this patent is extended or adjusted under 35 U.S.C. 154(b) by 134 days.

(21) Appl. No.: 16/048,859

(22) Filed: Jul. 30, 2018

(65) Prior Publication Data

US 2020/0029885 A1    Jan. 30, 2020

(51) Int. Cl.
*A61B 5/00*     (2006.01)
*H04B 1/38*     (2015.01)
*A61B 5/12*     (2006.01)
*A61B 3/10*     (2006.01)
*A61B 5/11*     (2006.01)

(52) U.S. Cl.
CPC .............. *A61B 5/4076* (2013.01); *A61B 3/10* (2013.01); *A61B 5/1112* (2013.01); *A61B 5/125* (2013.01); *A61B 5/4803* (2013.01); *A61B 5/742* (2013.01); *A61B 5/7405* (2013.01); *A61B 5/7455* (2013.01); *A61B 5/7475* (2013.01); *H04B 1/38* (2013.01); *A61B 2562/0219* (2013.01); *A61B 2562/0223* (2013.01); *A61B 2562/06* (2013.01)

(58) Field of Classification Search
CPC .... A61B 2562/0219; A61B 2562/0223; A61B 2562/06; A61B 3/10; A61B 5/1112; A61B 5/125; A61B 5/4076; A61B 5/4803; A61B 5/7405; A61B 5/742; A61B 5/7455; A61B 5/7475; H04B 1/38
See application file for complete search history.

(56) References Cited

U.S. PATENT DOCUMENTS

| | | |
|---|---|---|
| 6,669,481 B2 | 12/2003 | Winter et al. |
| 7,347,818 B2 | 3/2008 | Simon |
| 7,837,472 B1 | 11/2010 | Elsmore et al. |
| 8,478,394 B2 | 7/2013 | Prichep et al. |
| 8,568,311 B2 | 10/2013 | Laplaca et al. |
| 8,838,227 B2 | 9/2014 | Causevic et al. |

(Continued)

FOREIGN PATENT DOCUMENTS

| | | |
|---|---|---|
| WO | 2012071544 A3 | 11/2013 |
| WO | 2016179370 A1 | 11/2016 |

*Primary Examiner* — George Manuel
(74) *Attorney, Agent, or Firm* — Naval Information Warfare Center, Pacific; Kyle Eppele; J. Erie Anderson

(57) ABSTRACT

A handheld radio device that incorporates within equipment typically carried by a first-responder but with added functionality which enables assessments of a subject's cognitive, auditory, visual, and speech function. In addition to providing two-way tactical radio functionality, the handheld radio device operates to generate haptic, audible, and visual stimuli, and then assess a subject utilizing the handheld radio device based on the subject's responses to the stimuli on the interfaces and sensors of the handheld radio device. Because this functionality is provided in equipment this is already typically carried by the first-responder, assessments that are more forward-deployed and closer to the point and time of injury, exposure, or period of interest can occur.

19 Claims, 1 Drawing Sheet

(56) References Cited

U.S. PATENT DOCUMENTS

| | | |
|---|---|---|
| 9,039,631 B2 | 5/2015 | Kiderman et al. |
| 9,451,915 B1 | 9/2016 | Wong et al. |
| 9,883,831 B1 | 2/2018 | Stewart et al. |
| 2005/0053904 A1 | 3/2005 | Shephard et al. |
| 2005/0142524 A1 | 6/2005 | Simon et al. |
| 2005/0187436 A1 | 8/2005 | Doniger et al. |
| 2006/0240393 A1 | 10/2006 | Reeves et al. |
| 2006/0271640 A1 | 11/2006 | Muldoon et al. |
| 2007/0027406 A1 | 2/2007 | LaPlaca et al. |
| 2008/0004509 A1 | 1/2008 | Sahakian et al. |
| 2008/0187894 A1 | 8/2008 | Cady |
| 2009/0155754 A1 | 6/2009 | Shankle et al. |
| 2010/0221688 A1 | 9/2010 | Reeves et al. |
| 2010/0240016 A1 | 9/2010 | Ween et al. |
| 2012/0214143 A1 | 8/2012 | Severson et al. |
| 2012/0238831 A1 | 9/2012 | Benford |
| 2012/0330178 A1 | 12/2012 | Kraft et al. |
| 2012/0330182 A1 | 12/2012 | Alberts et al. |
| 2013/0006064 A1 | 1/2013 | Reiner |
| 2013/0018592 A1 | 1/2013 | Mollicone et al. |
| 2013/0035613 A1 | 2/2013 | Curtiss |
| 2013/0046206 A1 | 2/2013 | Preminger |
| 2013/0184603 A1 | 7/2013 | Rothman |
| 2013/0209977 A1 | 8/2013 | Lathan et al. |
| 2014/0074267 A1 | 3/2014 | Alberts et al. |
| 2014/0107429 A1 | 4/2014 | Simkovich et al. |
| 2014/0267196 A1* | 9/2014 | Villarreal ............... G02B 26/02 345/204 |
| 2014/0316221 A1 | 10/2014 | Rothman |
| 2014/0318699 A1* | 10/2014 | Longinotti-Buitoni ...................... A61B 5/0002 156/247 |
| 2015/0094622 A1 | 4/2015 | Curtiss |

* cited by examiner

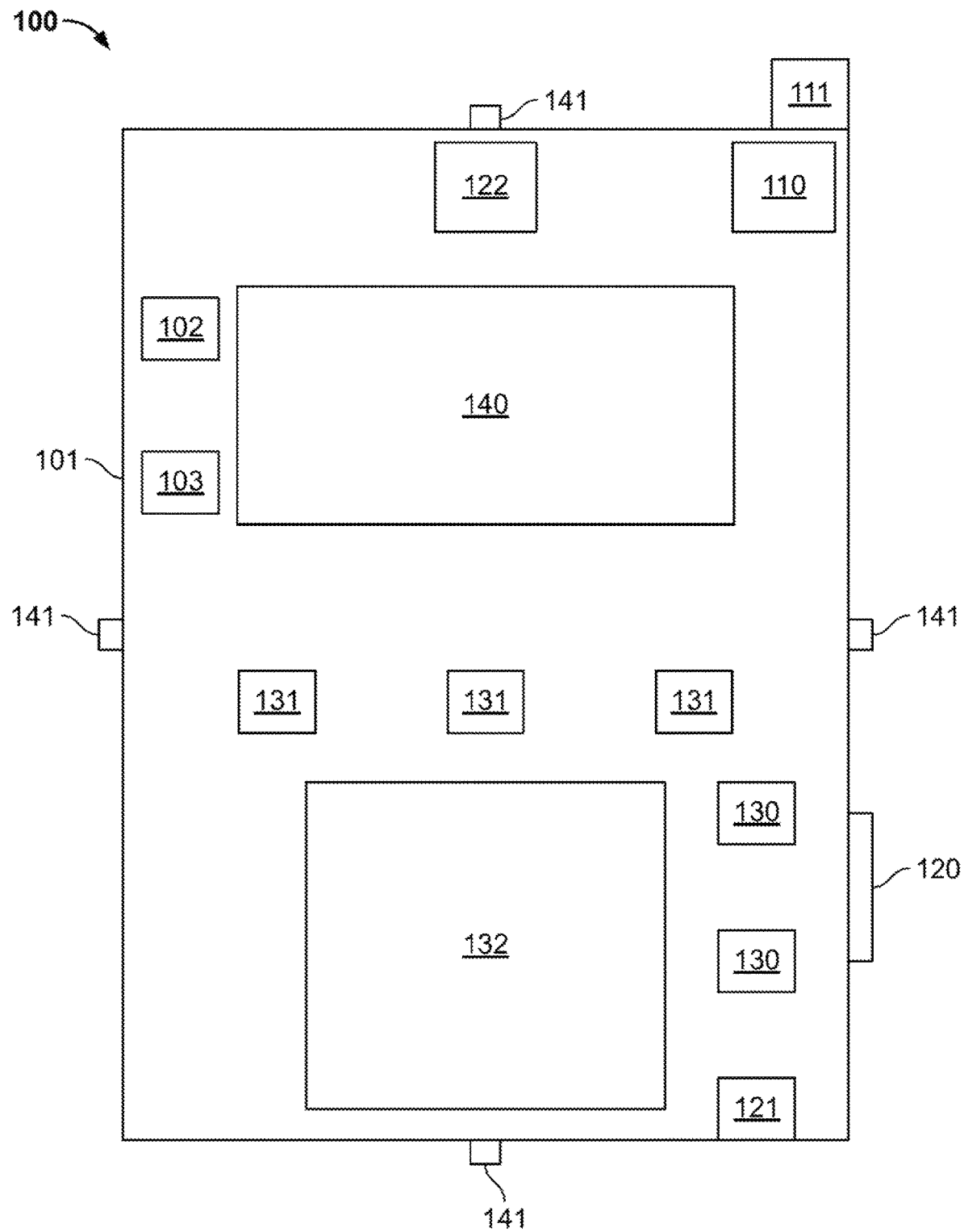

HANDHELD RADIO DEVICE FOR ASSESSING COGNITIVE, AUDITORY, VISUAL, AND SPEECH FUNCTION

STATEMENT OF GOVERNMENT INTEREST FEDERALLY SPONSORED RESEARCH AND DEVELOPMENT

The United States Government has ownership rights in this invention. Licensing inquiries may be directed to Office of Research and Technical Applications, Space and Naval Warfare Systems Center, Pacific, Code 72120, San Diego, Calif. 92152; telephone (619) 553-5118; email: ssc_pac_t2@navy.mil. Reference Navy Case No. 103692.

BACKGROUND OF THE INVENTION

Field of the Invention

This invention relates generally to a communication and testing apparatus and, more particularly, to a handheld radio operative to enable assessments of a subject's cognitive, auditory, visual, and speech function.

Description of the Prior Art

The ability for rapid human cognitive, auditory, visual, or speech assessment by medical first responders following a subject's exposure to, and injury from, a blast, concussive event, stressor, or other traumatic event to the body or brain's auditory, visual, or speech systems is dependent on the availability of testing resources and measurement instrumentation in a field or operational environment, as well as the speed in which those resources and tools are deployed, utilized, and administered. Essentially, the more forward-deployed and closer to the point and time of injury, exposure, or period of interest, the more applicable such data is for non-diagnostic assessment purposes.

The nature of these fields or operational environments in which a subject is often exposed to traumatic events impose limitations on the weight, power supply, and form factor of the tools available to first responders. Thus, there is limited opportunity for first responders in the medical community to stock or provision the additional ambulatory hardware and software necessary to make these measurements and assessments.

Thus, there remains a need for an improved radio device that allows a first responder to assess a subject's cognitive, auditory, visual, and speech function at a moment that is proximal to the time of injury, exposure, or other period of interest.

SUMMARY OF THE INVENTION

The present disclosure describes a handheld radio device that incorporates within equipment typically carried by the first-responder but with added functionality which enables assessments of a subject's cognitive, auditory, visual, and speech function. In accordance with one embodiment of the present disclosure, a handheld radio device includes: a body that includes at least an internal controller and an internal battery, wherein said body includes an integral microphone, vibrator, accelerometer, gyroscope, magnetometer, and global positioning system interface which are each operatively connected to said controller; a communications system integral with said body and connected to said controller, wherein said handheld radio device is configured to provide two-way tactical radio communication functionality that utilizes multiple VHF/UHF or cellular frequency bands through said communications system; a user talk interface integral with said body and connected to said controller, wherein said user talk interface is adapted to activate the microphone in response to predetermined action from a user; a sound interface integral with said body and connected to said controller, wherein said handheld radio device is configured to transduce electrical audio signals with said sound interface; at least one mechanical tactile interface integral with said body and connected to said controller, wherein said at least one mechanical tactile interface is adapted to generate electrical input signals in response to physical contact from a user with the at least one mechanical tactile interface; a display interface integral with said body and connected to said controller, wherein said handheld radio device is configured to generate at least one selected visual output by said display interface; at least one visual indicator integral with said body and connected to said controller, wherein said at least one visual indicator is adapted to modify its visual appearance in response to an electrical output signal from the controller; and wherein said handheld radio device is configured to generate sensory stimuli through at least one of the vibrator, sound interface, the display interface, and at least one visual indicator as well as assess a subject utilizing the handheld radio device based on at least one of (1) an interaction by the subject with at least one of the microphone and the at least one mechanical tactile interface and (2) a real time status of the accelerometer, gyroscope, magnetometer, and global positioning system interface following the generation of sensory stimuli.

BRIEF DESCRIPTION OF THE DRAWINGS

FIG. 1 is a schematic showing the basic components of a handheld radio device built in accordance with the present application.

DETAILED DESCRIPTION OF THE INVENTION

Described herein is a handheld radio device which incorporates a cognitive, auditory, visual, and speech assessment application that is executable from a radio apparatus as either individual assessments or a battery of assessments, as selected by an administrator user. The present handheld radio device allows an administrator user to collect cognitive, auditory, visual, and speech performance data using a radio apparatus of the type that the user typically already carries. Thus, the user does not have to carry a separate portable computer and/or tablet/handheld computer device in addition to the user's radio apparatus. Additionally, the present handheld radio device allows for the wireless transmission of data for analysis and storage using the handheld radio device's existing communication capabilities.

Referring now to FIG. 1, the handheld radio device 100 includes a ruggedized body 101 that is compliant with, or similar to, the United States Military Standard of Environmental Engineering Considerations and Laboratory Tests (MIL-STD-810) standard, and utilizes common specifications for battery and other external accessories. The handheld radio device 100 includes at least an internal controller 102 operative to control the operation of the internal and external components of the handheld radio device 100 and an internal battery 103 operative to supply electricity to the electrically operated components of the handheld radio device 100. In lieu of an internal battery 103, the battery may be attached to the handheld radio device 100. The handheld radio device 100 additionally may include a vibrator, an accelerometer, a gyroscope, a magnetometer, and a global positioning system ("GPS") interface housed in said body and connected to said controller 102.

The handheld radio device 100 has a communications system that implements the functionality of existing military, government, or first responder two-way tactical radio communication devices that utilize multiple VHF/UHF or cellular frequency bands, and may utilize a software defined radio architecture. The communications system includes a full- or half-duplex radio communications transceiver 110 as well as an antenna 111. The antenna 111 may be defined by a whip or telescoping antenna extending distally from the radio's form factor, while in others the antenna 111 is replaced via a common connector to a corded external antenna.

The radio's primary communication transmission method will be via mechanical push-to-talk ("PTT") methods by utilizing a user talk interface 120 which may be defined by a physical momentary switch button located on the radio's body to activate an integrated microphone 121 when pressed. The user talk interface 120 may also be defined by an externally corded or wireless PTT device. In either implementation, the user talk interface 120 may or may not utilize voice-operated transmit ("VOX") or switch technology.

Electrical audio signal is transduced utilizing a sound interface 122, which may be defined by an integrated loudspeaker on the radio's body. Alternatively, sound interface may be defined by an externally connected loudspeaker. It is contemplated that the sound interface 122 may be either independent from the radio's microphonics, or a part of a headset microphone/headphone combination.

Mechanical tactile interfaces of the handheld radio device 100 include external tuning knobs 130 and switches 131 for the control of volume, channels, frequencies, or squelch. Mechanical tactile interfaces may also include integrated input switches using non-capacitive buttons on an integrated silicone rubber, plastic, or metallic keypad 132.

The handheld radio device 100 also includes a display interface 140 integrated to the radio's body. The display interface 140 employs non-capacitive sensing display features, utilizing thin-film optics, including liquid crystal displays ("LCD"), segment displays, dot-matrix displays, or light-emitting diode ("LED") displays (traditional or organic).

The handheld radio device 100 additionally includes a plurality of visual indicators, including light indicators 141. Alternatively, other visual-cueing mechanisms may be employed.

Utilizing an embedded software-defined radio architecture and an assessment software application, the handheld radio device 100 is operative to employ cognitive, auditory, visual, and speech assessments, as either individual assessments or a battery of assessments, as selected by the user administrator. All or some of the assessment software application may be programmed into or otherwise stored on the handheld radio device 100 or may be accessible to the handheld radio device 100 through a computer network to which the handheld radio device 100 can connect.

Through the various user interfaces of the handheld radio device 100, a subject undergoing assessment will interact with the handheld radio device 100, receiving visual and auditory prompts and stimuli presented through the handheld radio device's 100 sound interface 122 (whether the integrated loudspeaker, connected speaker, or both), display interface 140, associated light indicators 141, other visual-cueing mechanisms, or vibratory output haptics. In response, subject undergoing assessment will provide responses to stimuli via the handheld radio device's 100 integrated keypad 132, the handheld radio device's 100 external tuning knobs 130 and switches 131, the microphone 121, and the integrated accelerometer, gyroscope, magnetometer, or GPS. Administration directions are provided verbally by the human administrator user or by auditory and visual directions delivered by the handheld radio device itself using the speaker or display. The handheld radio device 100 administers these specific cognitive, auditory, visual, and speech assessments to measure the person's current performance on those measures. Specifically, these include the following:

Cognitive: Using classic neuropsychological and neurocognitive testing paradigms for the measurement of vigilance, memory (working, procedural, etc.), attention, reaction time, and others, the handheld radio device 100 will deliver stimuli as testing prompts to the user through the various modalities, then collect, record, and analyze a response to those stimuli, looking for cognitive performance change. Stimuli will be presented via the handheld radio device's 100 display interface 140, sound interface 122, or light indicators 141, with user response provided through keypad 132, knobs 130, dials (not shown), or microphone 121. Motor and tactile performance would be assessed through feedback provided by the subject manipulating the handheld radio device's 100 accelerometer, gyroscope, magnetometer, or GPS positioning inputs.

Auditory: Auditory performance, including hearing, assessment of the user will be assessed through the presentation of auditory stimuli via the handheld radio device's 100 sound interface 122 (which could be the integrated loudspeaker, the connected speaker, or a pair of connected speakers embodied as headphones) to the human ear, either independently or simultaneously (one ear or both). Comprehension or detection of these auditory cues by the user will be indicated by input provided back to the handheld radio device 100 by the user through either the mechanical tactile interfaces, or auditory prompts to the microphone 121. The handheld radio device 100 will also query ambient surrounding noises via the microphone 121 to determine what amount of noise to subtract, as well as determining at which volume the stimuli should be presented.

Visual: Utilizing the apparatus' physical components that emit visual cues, the handheld radio device 100 will test and measure the user's visual system at the time of testing. Using different colored LED and LCD screens that are already part of the handheld radio device 100 for its radio and communication purpose, the handheld radio device 100 will present different colors or tones with varying levels of contrast and brightness and times to the user to assess visual performance.

Speech: Utilizing the handheld radio device's 100 hardware, the speech assessment process will open the microphone 121 device to listen for speech input from the person being assessed or tested following a prompt or directions to do so. The handheld radio device 100 will then perform onboard analysis of the recorded voice, recognizing signs or indices of dysarthria, dysprosody, or other possible injury to either the physical speech system, or the corresponding speech centers of the brain.

Following test assessment administration, the handheld radio device 100 will internally calculate basic descriptive and linear statistics, present them through the handheld radio device's 100 display interface 140 and/or the sound interface 122, archive them locally on the handheld device 100, as well as transmit the data wirelessly to a remote device or location using the handheld radio device's 100 existing radio communication infrastructure of data ports, channels, and protocols.

It will be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:

1. An apparatus for assessing cognitive, auditory, visual, and/or speech function, consisting of:
    a handheld, two-way tactical radio having a software-defined radio architecture and a physical momentary switch button located on a body of the radio for push-to-talk functionality; and
    an assessment software application programmed into the radio and configured to perform cognitive, auditory, visual, and speech assessments of a user of the radio based on the user's reaction to sensory stimuli generated by the radio.

2. The apparatus for assessing cognitive, auditory, visual, and/or speech function of claim 1, wherein the radio is compliant with the United States Military Standard of Environmental Engineering Considerations and Laboratory Tests (MIL-STD-810) standard.

3. The apparatus for assessing cognitive, auditory, visual, and/or speech function of claim 2, wherein the user's reaction includes interacting with a button, a knob, and a microphone of the radio.

4. A method for assessing cognitive, auditory, visual, and/or speech function of a user using a handheld, two-way, tactical radio having a software-defined radio architecture comprising the following steps:
    selectively generating sensory stimuli with the following radio features: a vibrator, a sound interface, a display interface, and a visual indicator, wherein the radio is primarily used for two-way communication; and
    assessing the user's cognitive, auditory, visual, and speech functions based only on the user's interaction with the radio following the generation of the sensory stimuli.

5. The method of claim 4, wherein the radio further comprises an accelerometer, and wherein the assessing step is further based on a real time status of the accelerometer following the generation of sensory stimuli.

6. The method of claim 5, wherein the radio further comprises a gyroscope, a magnetometer, and a global positioning system, and wherein the assessing step is further based on a real time status of the radio's accelerometer, gyroscope, magnetometer, and global positioning system following the generation of sensory stimuli.

7. The method of claim 6, further comprising:
    using classic neuropsychological and neurocognitive testing paradigms for the measurement of vigilance, memory, attention, and reaction time of the user;
    collecting data via the radio representative of the user's response to the sensory stimuli;
    identifying cognitive performance change based on the collected data, wherein the user's motor and tactile performance; and
    assessing the user's motor and tactile performance through feedback provided by the user's manipulation of the radio following the generation of the sensory stimuli.

8. The method of claim 7, further comprising presenting auditory stimuli via the radio's sound interface to the user.

9. The method of claim 8, further comprising:
    recording an ambient noise level with the radio; and
    determining, based on the recorded ambient noise level, a volume at which to present the auditory stimuli to the user.

10. The method of claim 9, further comprising:
    recording audible feedback from the user after the step of presenting the auditory stimuli to the user; and
    subtracting an amount of noise from the recorded audible feedback based on the recorded ambient noise level.

11. The method of claim 8, further comprising presenting to the user visual cues with varying levels of contrast and brightness at various times on a screen of the radio.

12. The method of claim 11, wherein the step of presenting visual cues to the user further comprises presenting different colors.

13. The method of claim 11, further comprising:
    recording audible feedback from the user after the step of generating the sensory stimuli;
    performing with the radio an onboard analysis of the audible feedback such that signs or indices of dysarthria, dysprosody, or other possible injury to either the user's physical speech system, or the corresponding speech centers of the user's brain are recognized.

14. The method of claim 13, further comprising:
    calculating with the radio basic descriptive and linear statistics based on the user's assessed cognitive, auditory, visual, and speech functions;
    archiving the basic descriptive and linear statistics within the radio; and
    transmitting the user's assessed cognitive, auditory, visual, and speech functions wirelessly to a remote location using the radio's existing radio communication infrastructure of data ports, channels, and protocols.

15. The method of claim 4, wherein the radio further comprises a gyroscope, and wherein the assessing step is further based on a real time status of the gyroscope following the generation of sensory stimuli.

16. The method of claim 4, wherein the radio further comprises a magnetometer, and wherein the assessing step is further based on a real time status of the magnetometer, following the generation of sensory stimuli.

17. The method of claim 4, wherein the radio further comprises a global positioning system, and wherein the assessing step is further based on a real time status of the global positioning system following the generation of sensory stimuli.

18. The method of claim 4, further comprising the step of providing, through the radio, prior to the generation of sensory stimuli, administration directions to the user regarding an upcoming cognitive, auditory, visual, or speech function assessment.

19. The method of claim 4, further comprising:
    transmitting the user's assessed cognitive, auditory, visual, and speech functions wirelessly to a remote location using the radio's existing radio communication infrastructure of data ports, channels, and protocols.

* * * * *